United States Patent [19]

Blackmore et al.

[11] Patent Number: 4,585,455
[45] Date of Patent: Apr. 29, 1986

[54] INTRAOCULAR LENS WITH IRIS SPACER MECHANISM

[75] Inventors: John M. Blackmore, Redwood City; Timothy Bittner, Duarte, both of Calif.

[73] Assignee: Ioptex Inc., Azusa, Calif.

[21] Appl. No.: 546,435

[22] Filed: Oct. 28, 1983

[51] Int. Cl.⁴ .............................................. A61F 2/16
[52] U.S. Cl. ................................................ 623/6
[58] Field of Search ............................................... 3/13

[56] References Cited

U.S. PATENT DOCUMENTS 4,370,760 2/1983 Kelman .................................... 3/13
4,442,553 4/1984 Hessburg .................................. 3/13

OTHER PUBLICATIONS

Lens Styles from Cilco, advertisement brochure Cilco, 6 pages, Cilco, Inc., 1616 13th Ave., Box 1680, Huntington, West Virginia 25717, p. 2 relied upon, Oct. 1982.

Primary Examiner—Ronald L. Frinks
Attorney, Agent, or Firm—Bielen & Peterson

[57] ABSTRACT

An intraocular lens utilizing an optical portion and having at least one appendage with a first end portion connected to the optical portion. A second end portion of the appendage is intended for contacting the periphery of the eye. The terminus of the second end portion of the appendage includes a spacer which is positioned between the terminus of the appendage and the iris. An intermediate portion of the appendage connects the first and second end portions of the appendage.

7 Claims, 6 Drawing Figures

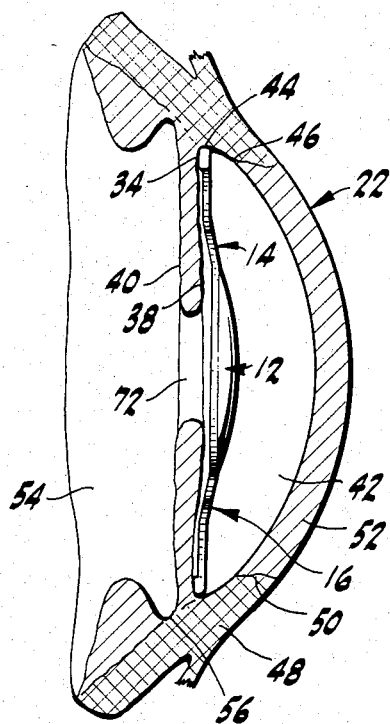

INTRAOCULAR LENS WITH IRIS SPACER MECHANISM

BACKGROUND OF THE INVENTION

The present invention relates to a novel intraocular lens which is especially useful for placement in the eye adjacent the iris.

Prior art intraocular lenses such as the intraocular lens shown in the U.S. Pat. No. 4,174,543 have been used in the anterior chamber of the eye to correct aphakia following cataract surgery. It has been found to be very important for an intraocular lens implanted within the eye to avoid contacting the iris. The constriction and dilation of the pupil results in irritation to the iris where an intraocular lens is touching a portion of the iris surrounding the pupil. Also, a synache may develop at the peripheral portion of the intraocular lens at the angle of the eye. In other words, tissue may grow and entrap the end of the intraocular lens at the angle of the eye. This will cause the intraocular lens to bind which may damage the endothelium layer of the cornea.

An intraocular lens which minimizes contact with the iris would be an achievement in the medical field.

SUMMARY OF THE INVENTION

In accordance with the present invention a novel intraocular lens structure is provided which solves the problems associated with iris irritation.

Lens of the present invention employs an optical portion which is properly determined to correct the vision of the patient. Connected to the optical portion is at least one appendage which has a first end portion connected to the end portion and extending away from the optical portion. A second end portion which is intended for contacting the periphery of the eye includes a spacer which is positioned between the terminus of the appendage and the iris. An intermediate portion connects to the first and second end portions of the appendage.

The second end portion spacer may be one of a pair of spacers. In other words, a pair of spacers may lie on the end of the second appendage but spaced from one another laterally in relation to the lens portion. In this case, a connecting member would lie between the first and second spacers.

The appendage first portion may set substantially in a first plane and the second portion of the appendage may set substantially in a second plane which intersects the first plane. Moreover, the appendage intermediate portion may include an open loop which sets partially in the first plane of the first end portion and partially in the second plane of the second end portion of the appendage. Finally, the lens portion itself may lie in a third plane which intersects the first plane of the first portion of the appendage. The result is a vaulted intraocular lens which positions such that the lens and the first portion of the appendage, including a part of the intermediate portion of the appendage would separate a distance from the iris. The second portion and a part of the intermediate portion of the appendage of the intraocular lens would also be away from the iris because of the spacer mechanism found on the terminus of the appendage.

It may be apparent that a novel intraocular lens has been described. It is therefore an object of the present invention to provide an intraocular lens which may be used in the anterior chamber of the eye following cataract surgery.

It is another object of the present invention to provide an intraocular lens which minimizes iris irritation due to iris touch.

It is another object of the present invention to provide an intraocular lens which may be implanted in the anterior chamber of the eye and which includes a structure to prevent entrapment of the lens appendage by a synache type growth.

The invention possesses other objects and advantages especially as concerns particular characteristics and features thereof which will become apparent as the specification continues.

BRIEF DESCRIPTION OF THE DRAWINGS

FIG. 1 is a top plan view of the lens of the present invention showing a portion of the eye schematically.

FIG. 2 is a side elevational view of the lens of the present invention.

FIG. 3 is an end elevational view of the lens of the present invention.

FIG. 4 is a sectional view of a human eye showing the lens of the present invention in place within the anterior chamber of the eye.

FIG. 5 is a side elevational view of another embodiment of the lens of the present invention.

FIG. 6 is a top plan view of the embodiment of the lens of the present invention shown in FIG. 5 with portions of the anatomy of the eye shown schematically.

For a better understanding of the invention reference is made to the following detailed description of the preferred embodiments of the invention which should be referenced to the hereinabove described drawings.

DESCRIPTION OF THE PREFERRED EMBODIMENTS

Various aspects of the present invention will evolve from the following detailed description of the preferred embodiments should be referenced to the hereinabove described drawings.

The first embodiment of the lens of the present invention is denoted by reference character 10. Intraocular lens 10 includes a lens portion or zone 12 which may be formed of polymethylmethacrylate (PMMA). The lens portion 12 has an optical axis (not shown) normal to the plane of the lens portion 12. Lens 10 includes first and second arms or appendages 14 and 16 which extend from and are connected to lens portion 12.

Appendages 14 and 16 are essentially identical in construction, although being attached to opposite parts of lens portion 12. Both appendages may be constructed of polypropylene or other suitable material known in the art. The following description for appendage 14 will also suffice for appendage 16. Appendage 14 includes a first end portion 18 which is connected to the optical portion 12 and extends outwardly away from the same. A second end portion 20 includes a terminus 44 which contacts the periphery of the eye 22 generally at points 24 and 26. Intermediate portion 28 connects first end portion 18 with second end portion 20. Intermediate portion 28 may possess loops 30 and 32 which adds to the resiliency of appendage 14.

Second end portion 20 includes a pair of pedstals or spacers 34 and 36. Each spacer 34 and 36 is thicker than the remaining portions of appendage 14 and comprises a solid mass extending from and unitary with the terminus 44. The spacers 34, 36 extend transverse to the second end portion 20 and terminus 44 in a direction parallel to the optical axis of lens portion 12 and terminate at a location spaced outwardly from said end portion 20 and terminus 44. This is best shown in FIGS. 2 and 3, the latter being designated to show appendage 14 rather than appendage 16 for the sake of clarity.

The intraocular lens 10 may be vaulted in that the first portion 18 and the second portion 20 lie in intersecting planes. It should be noted that intermediate portion 28 lies partially in either plane. Also, the plane of lens portion 12 intersects the plane of first portion 18. Turning to FIG. 4 it may be seen that this vaulting permits first portion 18 and second portion 20 of appendage 14 to lie away from the surface 38 of iris 40. The same is true for appendage 16 on the opposite side of the anterior chamber 42. The spacers 34 and 36 also prevent appendage 14 from touching iris 40 toward the periphery of eye 22. As shown in FIG. 4, the terminus 44 of appendage 14 fits into angle 46 which is the meeting place between the sclera 48 and the iris 40. It should be noted that angle is hidden by an extension 50 of sclera 48 which meets the clear cornea 52. A connecting member 53 between spacers 34 and 36 would not necessarily contact angle 46, FIG. 1. Although tissue may grow to spacers 34 and 36 the thickness and transverse dimension of spacers 34 and 36 prevent entrapment by such tissue growth and thereby prevent the binding of appendage 14 in the angle area.

Although lens 10 may be employed in the anterior chamber 42 of eye 22 the same lens may also be placed in the posterior chamber 54 and be placed in the ciliary sulcus 56.

Turning FIGS. 5 and 6 another embodiment of the present invention is shown and designated by character 10A. Intraocular lens 10A includes lens portion 12 and a pair of appendages 58 and 60 as with the prior embodiment both appendages are essentially identical although attached in different areas to lens 12. The description for appendage 58 will suffice for appendage 60. Appendage 58 includes a first portion 62 connected to lens portion 12 and an intermediate portion 64 connected thereto. Second end portion 66 is intended for contacting the periphery of the eye at angle 46 and is provided with spacer 68 and 70. A connecting member 72 spans the distance between 68 and 70 and is recessed more than connecting member 53 of appendage 3, FIG. 1.

In operation, the surgeon would implant intraocular lens 10 or 10A in the anterior or posterior chamber of eye 22. The spacers 34 and 36 found on second end portion 20 of appendage 14 and the spacers shown on appendage 16 would separate those appendages from iris 40 at the peripheral portions of lens 10. The vaulting provided by the arrangement of first end portion 18 in relation to second end portion 20 and the plane of lens portion 12 would vault the reminder of lens 10 away from the iris 40 near the pupil 72. Thus, intraocular lens 10 or 10A would be easily fitted into the anterior chamber 42 of eye 22 and not be entraped or bound by tissue at the angle area 46 of eye 22. This would prevent any dislocation of lens 10 or 10A and prevent endothelial touch.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An intraocular lens for implantation in an eye comprising:
    a. a lens portion having an optical axis; and
    b. at least one appendage having a first end portion connected to said lens and extending outwardly therefrom, a second end portion including a terminus which is intended for contacting the periphery of the eye, said second end portion including a spacer for positioning between said terminus of said at least one appendage and the iris and positioned along said at least one appendage from said terminus toward said first end portion, said spacer comprising a solid mass being unitary with and extending from said terminus of said second end portion, said terminus and said spacer being free of openings therebetween, said spacer having a thickness extending transverse to said end portion and terminus in a direction parallel to said optical axis and terminating at a location spaced outwardly from said end portion and terminus and an intermediate portion connecting said first and second end portions.

2. The intraocular lens of claim 1 which includes a pair of spacers connected to said second end portion of said at least one appendage, said pair of spacers being separated by a connecting member.

3. The intraocular lens of claim 1 in which said first end portion of said at least one appendage may be substantially in a first plane and the second end portion of said at least one appendage may lie substantially in a second plane which intersects said first plane.

4. The intraocular lens of claim 3 in which said intermediate portion includes an open loop.

5. The intraocular lens of claim 4 in which said intermediate portion lies partially in said first plane of said first end portion and partially in said second plane of said second end portion.

6. The intraocular lens of claim 3 in which said lens portion lies substantially in a third plane which intersects said first plane of said first end portion.

7. The intraocular lens of claim 1 which further comprises a second appendage having a first end portion connected to said lens portion and extruding outwardly therefrom, a second end portion which is intended for contracting the periphery of the eye, said second end portion including a spacer positioned between said terminus of said at least one appendage and the iris, and an intermediate portion connecting said first and second end portion.

* * * * *